US009181401B2

(12) United States Patent
Parakka et al.

(10) Patent No.: US 9,181,401 B2
(45) Date of Patent: Nov. 10, 2015

(54) PHOSPHORYLCHOLINE-BASED AMPHIPHILIC SILICONES FOR MEDICAL APPLICATIONS

(75) Inventors: James Parakka, San Bruno, CA (US); Ananth V. Iyer, Emeryville, CA (US); Anfeng Wang, Fremont, CA (US); Xuwei Jiang, Albany, CA (US); Yuan Tian, Alameda, CA (US); Robert Ward, Orinda, CA (US)

(73) Assignee: DSM IP ASSETS B.V., Heerlen (NL)

( * ) Notice: Subject to any disclaimer, the term of this patent is extended or adjusted under 35 U.S.C. 154(b) by 202 days.

(21) Appl. No.: 13/378,260

(22) PCT Filed: Jun. 7, 2010

(86) PCT No.: PCT/US2010/037576
§ 371 (c)(1),
(2), (4) Date: Feb. 9, 2012

(87) PCT Pub. No.: WO2010/147779
PCT Pub. Date: Dec. 23, 2010

(65) Prior Publication Data

US 2012/0136087 A1 May 31, 2012

Related U.S. Application Data

(60) Provisional application No. 61/187,151, filed on Jun. 15, 2009.

(51) Int. Cl.

| | |
|---|---|
| ***A61L 15/24*** | (2006.01) |
| ***C08L 83/08*** | (2006.01) |
| ***G02B 1/04*** | (2006.01) |
| ***C08F 30/02*** | (2006.01) |
| ***C08F 230/02*** | (2006.01) |
| ***C07F 7/02*** | (2006.01) |
| ***C07F 9/02*** | (2006.01) |
| ***C08G 77/395*** | (2006.01) |
| ***A61L 31/10*** | (2006.01) |
| ***A61L 15/26*** | (2006.01) |
| ***C07F 9/6574*** | (2006.01) |
| ***A61L 27/34*** | (2006.01) |
| ***C08F 230/08*** | (2006.01) |
| ***C07F 9/09*** | (2006.01) |
| ***A61F 13/00*** | (2006.01) |
| ***A61L 27/18*** | (2006.01) |
| ***C08L 83/10*** | (2006.01) |
| ***A61L 26/00*** | (2006.01) |

(52) U.S. Cl.
CPC ........ *C08G 77/395* (2013.01); *A61F 13/00017* (2013.01); *A61L 15/26* (2013.01); *A61L 26/0019* (2013.01); *A61L 27/18* (2013.01); *A61L 27/34* (2013.01); *A61L 31/10* (2013.01); *C07F 9/091* (2013.01); *C07F 9/092* (2013.01); *C07F 9/65742* (2013.01); *C07F 9/65746* (2013.01); *C08F 230/08* (2013.01); *C08L 83/08* (2013.01); *C08L 83/10* (2013.01); *G02B 1/043* (2013.01); *C08F 230/02* (2013.01)
USPC ............................ 523/107; 526/277; 556/405

(58) Field of Classification Search
USPC ............................ 523/107; 526/277; 556/405
See application file for complete search history.

(56) References Cited

U.S. PATENT DOCUMENTS

| | | | | |
|---|---|---|---|---|
| 5,272,010 | A * | 12/1993 | Quinn | 428/411.1 |
| 6,183,083 | B1 * | 2/2001 | Ocampo | 351/159.65 |
| 6,346,594 | B1 * | 2/2002 | Watanabe et al. | 528/26 |
| 6,828,029 | B1 | 12/2004 | Lewis et al. | |
| 6,893,595 | B1 * | 5/2005 | Muir et al. | 264/255 |
| 2006/0020098 | A1 | 1/2006 | Miyazawa et al. | |
| 2007/0141104 | A1 | 6/2007 | Hauenstein | |
| 2008/0314767 | A1 | 12/2008 | Lai et al. | |
| 2009/0048423 | A1 | 2/2009 | Stopek | |
| 2009/0100801 | A1 | 4/2009 | Zhao et al. | |
| 2010/0262238 | A1 * | 10/2010 | Chen et al. | 623/11.11 |

FOREIGN PATENT DOCUMENTS

| | | | |
|---|---|---|---|
| EP | 0 989 138 | A2 | 3/2000 |
| JP | 2002-265532 | A | 9/2002 |
| JP | 2006-199749 | A | 8/2006 |
| WO | WO 2008/023604 | A1 | 2/2008 |

OTHER PUBLICATIONS

Machine translated JP 2006-199749 A1, Aug. 2008.*
Machine translated JP 2004/500458, Japan, 2004.*
Goda et al., "Biomimetic phoshorylcholine polymer grafting from polydimethylsiloxane surface using photo-induced polymerization", Biomaterials 27, (2006) pp. 5151-5160.
Huang et al., "Surface modification of silicone intraocular lens by 2-methacryloyloxyethyl phosphoryl-choline binding to reduce *Staphylococcus epidermidis* adherence", XP-002482517, Clinical and Experimental Ophthalmology 2007, 35, pp. 462-467.
Iwasaki et al., "Surface modification with well-defined biocompatible triblock copolymers Improvement of biointerfacial phenomena on a poly(dimethylsiloxane) surface", Colloids and Surfaces B: Biointerfaces 57 (2007), pp. 226-236.
Seo et al., "Surface tethering of phosphorylcholine groups onto poly(dimethylsiloxane) through swelling-deswelling methods with phospholipids moiety containing ABA-type block polymers", Biomaterials 29 (2008), pp. 1367-1376.
Yamada et al., "Synthesis of Novel Organopolysiloxanes Having a Phospholipid-like Structure", Macromolecules 28 (1995), Mar. 27, No. 7, pp. 2590-2591.
Office Action dated Jul. 15, 2014 for Japanese Application No. 2012-515011.

* cited by examiner

*Primary Examiner* — Tae H Yoon
(74) *Attorney, Agent, or Firm* — Birch Stewart Kolasch & Birch, LLP

(57) ABSTRACT

Amphiphilic biomimetic phosphorylcholine-containing silicone compounds for use in both topical and internal applications as components in biomedical devices. The silicone compounds, which include zwitterionic phosphorylcholine groups, may be polymerizable or non-polymerizable. Specific examples of applications include use as active functional components in ophthalmic lenses, ophthalmic lens care solutions, liquid bandages, wound dressings, and lubricious and anti-thrombogenic coatings.

11 Claims, No Drawings

PHOSPHORYLCHOLINE-BASED AMPHIPHILIC SILICONES FOR MEDICAL APPLICATIONS

This application is the National Phase under 35 U.S.C. 371 of PCT/US2010/037576 filed on Jun. 6, 2010, which claims priority under 35 U.S.C. 119(e) to U.S. Provisional Application No. 61/187,151 filed on Jun. 15, 2009, both of which are hereby expressly incorporated by reference into the present application.

FIELD OF THE INVENTION

The present invention is related to amphiphilic compositions of matter bearing zwitterionic components and their preparation. More specifically, this invention provides biomimetic phosphorylcholine-containing silicones for use in both topical and internal use as components in biomedical devices. The silicone compounds of the invention, which include zwitterionic phosphorylcholine groups, may be polymerizable or non-polymerizable. Specific examples of applications include use as active functional components in ophthalmic lenses, ophthalmic lens care solutions, liquid bandages, wound dressings, and lubricious and anti-thrombogenic coatings.

BACKGROUND OF THE INVENTION

Silicone hydrogels are currently widely used materials in ophthalmic lenses. Several brands are available in the commercial market place. While patient comfort has driven the market use of these lenses, the modality for use of these lenses depends on both the physical properties (including oxygen transport and lubricity of the lens) as well as the amount of undesired protein and lipid deposition on the lenses during wear. In a silicone hydrogel contact lens the oxygen transport property which has been correlated to lens comfort can be successfully accessed by using designed silicone and/or perfluorinated compounds while the wettability and or lubricity can be achieved by different methods of surface modification or by incorporation of hydrophilic components in the hydrogel composition. Different technologies exist today to present final silicone hydrogel lenses that have the optical clarity and desired lubricity with controllable modulus and high oxygen transmissibility.

Adsorption of unwanted components from the ocular tear fluid on to the lens material during wear is one of the contributing factors for reduced comfort experienced by patients. In addition, bacterial infections can potentially occur if lens care regimens are not followed for use of the lenses. The extent of undesirable adsorptions will determine the lens care needs for a specific lens and impact on the duration the ophthalmic lens can be present in the eye without causing blurring or discomfort.

Polymerizable antimicrobial silicone hydrogel compounds are of great utility in contact lens formulations to support new generation commercial ophthalmic lenses with reduced lens related infections and that is amenable to extended wear modality. The inherent antimicrobial activity presented by these compounds in an ophthalmic lens should lower the incidence of lens care related ocular infections in patients. Examples ranging from polymerizable quaternium silicone actives to the use of metal salts in lens formulations have been reported in literature, e.g., US 2007/0142583 A1 (Schorzman et al.); US 2008/0182956 A1 (Stanbro et al.); US 2008/0102122 A1 (Mahadevan et al.).

Another important feature that will support extended wear is the incorporation of compounds that show resistance to depositing undesirable proteins and lipids on to the lens. Zwitterionic components such as sulfobetaine and carboxybetaine derivatives have been incorporated in to a polymeric framework to yield coatings that resist protein adsorption with super-low fouling surfaces. See US 2008/011861 A1 (Shaoiyi et al.).

Biomimetic phosphorylcholine (PC) based polymers are known to show much superior anti-fouling properties. Phosphorylcholine based non-silicone hydrogel lenses are commercially available and show minimal protein and lipid spoliation after wear. See WO 92/07885 A1 (Bowers et al.) and Young et al., "Six month clinical evaluation of a biomimetic hydrogel contact lens," *The CLAO Journal,* 23(4):226-36 (1997). It has also been reported that silicone intraocular lens (IOL) surface modified by air plasma for binding 2-methacryloxyethyl phosphorylcholine (MPC), in addition to suppressing bacterial adhesion and colonization, improved the hydrophilicity of the IOL. Huang et al., "Surface modification of silicone intraocular lens by 2-methacryloyloxyethyl phosphorylcholine binding to reduce *Staphylococcus epidermidis* adherence," *Clinical & Experimental Ophthalmology,* 35:462-467 (2007). In another study, all four species of human pathogenic microorganisms that are often isolated in association with biomedical device-related infections—that is, *Staphylococcus aureus, Streptococcus mutans, Pseudomonas aeruginosa*, and *Candida albicans*—were found to have reduced propensity to bind to MPC-coated surfaces than to non-coated surfaces. This was attributed to the effect of "superhydrophilicity" of MPC-coated surfaces. Hirota et al., "Coating of a surface with 2-methacryloyloxyethyl phosphorylcholine (MPC) co-polymer significantly reduces retention of human pathogenic microorganisms," *FEMS Microbiology Letters,* 248:37-45 (2005).

The incorporation of phosphorylcholine moiety in to polymerizable silicone compounds combines the beneficial properties of high oxygen permeability of silicones and the lower protein adhesion, hydrophilicity, and antibacterial properties presented by the biostable phosphorylcholine (PC) entity. In addition to reduced protein adsorption, incorporation of PC in polymer systems has also been reported to provide anti-thrombogenic surfaces with reduced platelet adhesion and activations, suitable for use in medical devices. Ishihara et al., "Antithrombogenic polymer alloy composed of 2-methacryloyloxyethyl phosphorylcholine polymer and segmented polyurethane," *Journal of Biomaterials Science: Polymer Edition,* 11(11):1183-1195 (2000). Yoneyama et al., "The vascular prosthesis without pseudointima prepared by antithrombogenic phospholipid polymer," *Biomaterials,* 23:1455-1459 (2002).

Copolymers of 2-methacryloyl phosphorylcholine (MPC) with n-butylmethacrylate have been reported for use in both in a contact lens body as well as in packaging solutions. The lenses are capable of releasing the hydrophilic polymer from the contact lens for prolonged period of time and have been shown to reduce surface friction. See US 2009/0182067 A1 (Liu). Phosphorylcholine coated silicone hydrogels lenses have been reported to present a very wettable interface indicated by minimal hysterisis between the advancing and receding contact angle. While the uncoated silicone hydrogel show relatively low protein adsorption, the PC coated lenses enhances the effect producing a very low protein-fouling surface. Willis et al., "A novel phosphorylcholine-coated contact lens for extended wear use," *Biomaterials,* 22:3261-3272 (2001).

Silicone hydrogels—prepared both by random copolymerization of 2-methacryloyl phosphorylcholine (MPC) with bis (trimethylsiloxy)methylsilylpropyl glycerol methacrylate and as in interpenetrating network (IPN)—were shown to be hydrophilic as well as have protein adsorption resistance which is otherwise prevalent in silicone hydrogels. Superhydrophilic surfaces were achieved especially in the case of IPN based silicone hydrogels. Shimizu et al., "Super-hydrophilic silicone hydrogels with interpenetrating poly(2-methacryloxyethyl phosphorylcholine) networks," *Biomaterials,* 31:3274-3280 (2010).

Almost all the reported chemistries on the use of phosphorylcholine for ophthalmic applications centers on the use of MPC or copolymerization of this monomer with other components. Phase separation of MPC related polymers in a silicone hydrogel framework will need to be overcome to support optically clear ophthalmic lenses with desired functional properties. It is therefore of interest to design silicone monomers and oligomers with in-built phosphorylcholine moieties. The amphiphilic nature of these compounds makes them effective compatibilizers between the silicone and/or fluorinated hydrophobes and the hydrophilic components in a typical lens formulation. The use of such hybrid compounds in Silicone hydrogel formulations enable the formation of contact lenses with higher oxygen transmissibility coupled with superior wettability and reduced lens deposits in comparison to conventional silicone hydrogel lenses.

SUMMARY OF THE INVENTION

This instant invention provides novel polymerizable and non-polymerizable silicone compounds containing biomimetic phosphorylcholine (PC) groups for use in biomedical device applications that require high oxygen transmissibility and surfaces resistant to biofilm formation. The polymerizable compounds bearing phosphorylcholine disclosed in this invention find utility as monomers or crosslinkers in a contact lens formulation. The non-polymerizable compounds bearing PC groups may be used in the treatment of contact lenses to allow for slow release of PC-containing compounds for enabling reduced protein and lipid deposits and to enhance wettability and/or lubricity of the lenses. In addition, the non-polymerizable PC-containing silicone compounds can be used as formulation components in lens packaging and lens care solutions.

In one aspect, the present invention relates to phosphorylcholine-based amphiphilic silicones that comprise of one or more pendant phosphate groups covalently linked to an equivalent number of quaternary amine groups. These silicones are amphoteric, having both positive and negative charges on the same pendant group, and are amphiphilic by virtue of having hydrophilic and lipophilic groups within them.

This invention provides polymerizable silicone compounds having zwitterionic phosphorylcholine groups and one or more vinyl groups. In this embodiment, the silicone compound may comprise a silicone moiety having a weight average molecular weight of from 500 to 50,000 Daltons. The zwitterionic phosphorylcholine moiety may comprise a phosphate anion and an ammonium cation. The vinyl endgroup may be adjacent to a carbonyl group.

This invention also provides non-polymerizable silicone compounds comprising zwitterionic phosphorylcholine groups. In this embodiment, the silicone compound may comprise a silicone moiety having a weight average molecular weight of from 1000 to 1,500,000 Daltons and the zwitterionic phosphorylcholine endgroup comprises a phosphate anion and an ammonium cation.

The present invention provides multiple advantages to the hydrogel compositions made from the compounds of the invention, including high oxygen permeability, reduced protein adsorption, and lubricious surface properties. Furthermore, non-polymerizable variants bearing phosphorylcholine groups in accordance with the present invention find utility in contact lens packaging solution and lens care solutions, enabling reduced protein and lipid adsorption and enhanced wettability and/or lubricity of the lenses.

DETAILED DESCRIPTION OF THE INVENTION

The present invention provides non-polymerizable silicone compounds comprising a zwitterionic phosphorylcholine endgroup. A non-polymerizable silicone compound of this invention comprises a silicone moiety having a weight average molecular weight of from 1000 to 1,500,000 Daltons. The present invention also provides polymerizable silicone compounds which include in their molecules a zwitterionic phosphorylcholine endgroup and at least one vinyl endgroup. The vinyl endgroup and the zwitterionic endgroup may be present in separate endgroups of the silicones, or they may both be present in the same endgroup moiety. A polymerizable silicone compound of the present invention comprises a silicone moiety having a weight average molecular weight of from 500 to 50,000 Daltons. A vinyl group in the polymerizable silicone compound of the invention is adjacent to a carbonyl group. In both the polymerizable and the non-polymerizable silicone compounds of the present invention, the zwitterionic phosphorylcholine endgroup comprises a phosphate anion and an ammonium cation. The presence of the zwitterionic phosphorylcholine moiety (and the vinyl moiety) in the end groups of the silicone molecules provided by this invention facilitates their availability for the uses described hereinbelow. The term "endgroup" in this sense means at the end of the molecule or sufficiently close to the end of the molecule to facilitate location of the functional group at the surface of an article made from the molecule in question. In the case of the zwitterionic phosphorylcholine moiety, uses will include bio-affecting applications, while in the case of the vinyl group, uses will involve polymerization.

A silicone moiety in the polymerizable and the non-polymerizable silicone compounds of the present invention can be a silicone moiety having the average compositional formula $R^2_aR^3_bSiO_{(4-a-b)}/2$, wherein $R_2$ and $R_3$ are the same or different groups selected from alkyl, trialkylsiloxy, substituted silicone, alkoxy, alicyclic, and aromatic groups and the subscripts a and b are positive numbers that satisfy the conditions $0<a<3$, $0<b<3$, and $1<a+b<3$.

Suitable silicone moieties may be introduced into the polymerizable and non-polymerizable compounds of the invention from silicones including those of the formula $$R^{13}YR^{11}Si(R^{14}R^{15})O[Si(R^{16}R^{17})O]_r[Si(R^{27}R^{28})O]_tSi(R^{29}R^{30})R^{12}$$

in which:

$R^{14}$, $R^{15}$, $R^{16}$, $R^{17}$, $R^{27}$, $R^{28}$, $R^{29}$, and $R^{30}$, independently of one another, are $C_{1-8}$ alkyl, $C_{1-4}$ alkyl-substituted phenyl, $C_{1-4}$ alkoxy-substituted phenyl, fluoro($C_{1-18}$ alkyl), cyano($C_{1-12}$ alkyl), hydroxy-$C_{1-6}$ alkyl, amino-$C_{1-6}$ alkyl;

Y denotes —COO—, $CONR^{18}$—, —OCOO—, or —$OCONR^{18}$—, where each $R^{18}$ is independently H or $C_{1-7}$ alkyl;

$R^{11}$ denotes a divalent $C_{1-25}$ alkylene or $C_{6-30}$ arylalkylene radical, which may interrupted by —O—, —COO—, —$CONR^{18}$—, —OCOO— or —$OCONR^{18}$— and may comprise a hydroxy group, a primary, secondary, or tertiary amine group, a carboxy group, or carboxylic acid;

$R^{12}$ is a monovalent $C_{1-25}$ alkyl or $C_{6-30}$ aryl radical, which may interrupted by —O—, —COO—, —$CONR^{14}$—, —OCOO— or —$OCONR^{14}$— and may comprise a hydroxy group, a primary, secondary, or tertiary amine group, or a carboxy group;

$R^{13}$ is a monovalent $C_{1-25}$ alkyl or $C_{6-30}$ aryl radical, which comprises at least one hydroxy group, primary or secondary amine group, carboxy group, or site of olefinic unsaturation; and r and t independently of each other are an integer of up to 700 and (r+t) is from 5 to 700. Such monomers or macromere may include, for instance, 3-methacryloxypropyl-terminated-butyl-terminated-polydimethylsiloxane and (3-methacryloxy-2-hydroxypropyloxy)propyl-terminated-butyl-terminated-polydimethylsiloxane. Suitable monofunctionalized polysiloxanes are commercially available, e.g., from Aldrich Chemical Company and from GELEST of Morrisville, Pa.

Specific examples of siloxane-containing monomers which may be used to provide the silicone moieties in the compounds of the present invention include, without limitation, hydroxyl-terminated-polydimethylsiloxane, carboxypropyl-terminated-polydimethylsiloxane, carboxydecyl-terminated-polydimethylsiloxane, aminopropyl-terminated-polydimethylsiloxane, hydroxyalkyl-terminated-poly(propyleneoxy)polydimethylsiloxane, 3-methacryloxy propylpentamethyldisiloxane, bis(methacryloxypropyl)tetramethyl-disiloxane, N-[tris(trimethylsiloxy)silylpropyl]acrylamide, N-[tris(trimethylsiloxy)silylpropyl]methacrylamide, tristrimethylsilyloxysilylpropyl methacrylate, hydroxyethyleneoxypropylmethylsiloxane-(3,4-dimethoxyphenylpropyl)-methylsiloxane, N-[tris(trimethylsiloxy)silylpropylyl]methacrylamide, N-[tris(trimethylsiloxy)-silylpropyl]acrylamide, (3-methacryloxy-2-hydroxypropyloxy)propylbis(trimethylsiloxy)methylsilane-), (3-methacryloxy-2-hydroxypropyloxy)propyltris(trimethylsiloxy)silane, 3-methacryloxy-2-(2-hydroxyethoxy)propyloxy)propylbis(trimethylsiloxy)methylsilane, N-2-methacryloxyethyl-O-(methyl-bis-trimethylsiloxy-3-propyl)silyl carbamate, 1,3-bis[4-vinyloxycarbonyloxy)but-1-yl]tetramethyl-disiloxane, 3-(trimethylsilyl), propyl vinyl carbonate, 3-(vinyloxycarbonylthio)propyl-[tris(trimethylsiloxy)silane], 3-[tris(trimethylsiloxy)silyl]propylvinyl carbamate, 3-[tris(trimethylsiloxy)silyl]propyl allyl carbamate, 3-[tris(trimethylsiloxy)silyl]propyl vinyl carbonate, t-butyldimethylsiloxyethyl vinyl carbonate, trimethylsilylethyl vinyl carbonate, trimethylsilylmethyl vinyl carbonate, hydride-terminated-polydimethylsiloxane, and silanol-terminated-polydimethylsiloxane.

A polymerizable compound of the present invention may have the formula (I)

(I)

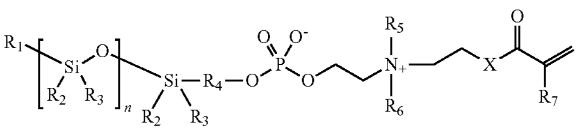

wherein: $R_1$ is an alkyl or alkoxy group of linear, branched, or cyclic structure, or an aromatic group, having up to 20 carbon atoms—preferably methyl, n-butyl, methoxy, or phenyl; $R_2$ and $R_3$ are the same or different groups selected from alkyl, trialkylsiloxy, substituted silicone, alkoxy, alicyclic, and aromatic groups—preferably methyl, n-butyl, methoxy, ethoxy, isopropoxy, or phenyl groups; n is a number of repeat silicone units from 1 to 700 units—preferably from 1 to 15 units; $R_4$ is an alkylene, polyether, perfluorinated polyether, carbamate, ester, amide, or urea linkage having up to 30 linking atoms—preferably an alkylene, polyether, or perfluorinated polyether linkage having up to 30 carbon and/or oxygen linking atoms; $R_5$ and $R_6$ are the same or different alkyl, alkoxy, or aromatic groups or alicyclic rings containing 3 to 6 carbon atoms—preferably methyl, n-butyl, methoxy, ethoxy, isopropoxy, or phenyl groups; $R_7$ is H or an alkyl group containing 1 to 6 carbon atoms; and X is O, NH, or N—$C_{1-6}$alkyl.

A specific example thereof includes compound 1:

1

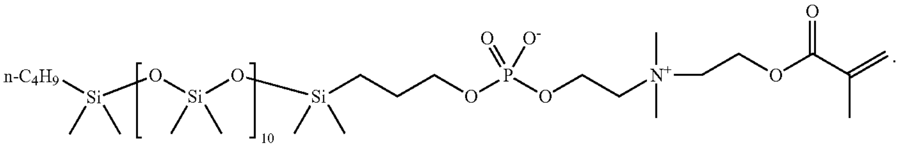

A polymerizable compound of the present invention may have the formula (II)

(II)

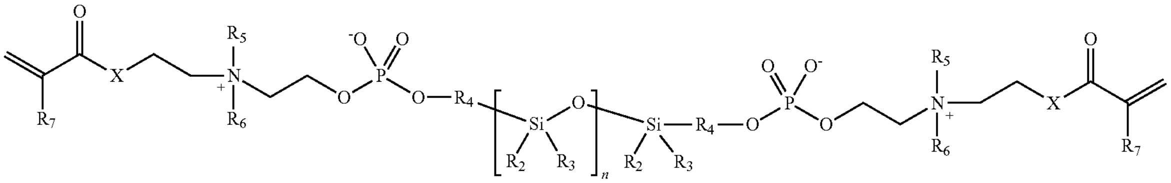

wherein: $R_2$ and $R_3$ are the same or different groups selected from alkyl, trialkylsiloxy, substituted silicone, alkoxy, alicyclic, and aromatic groups—preferably methyl, n-butyl, methoxy, ethoxy, isopropoxy, or phenyl groups; n is a number of repeat silicone units from 1 to 700 units—preferably 1 to 15 units; $R_4$ is an alkylene, polyether, perfluorinated polyether, carbamate, ester, amide, or urea linkage having up to 30 linking atoms—preferably an alkylene, polyether, or perfluorinated polyether linkage having up to 30 carbon and/or oxygen linking atoms; $R_5$ and $R_6$ are the same or different alkyl, alkoxy, or aromatic groups or alicyclic rings containing 3 to 6 carbon atoms—preferably methyl, n-butyl, methoxy, ethoxy, isopropoxy, or phenyl groups; $R_7$ is H or an alkyl group containing 1 to 6 carbon atoms; and X is O, NH, or N—$C_{1-6}$alkyl.

Specific examples thereof include compounds 2 and 4:

2

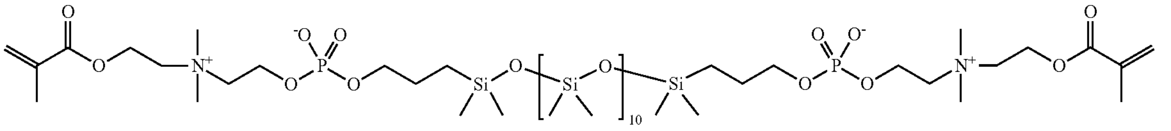

and

4

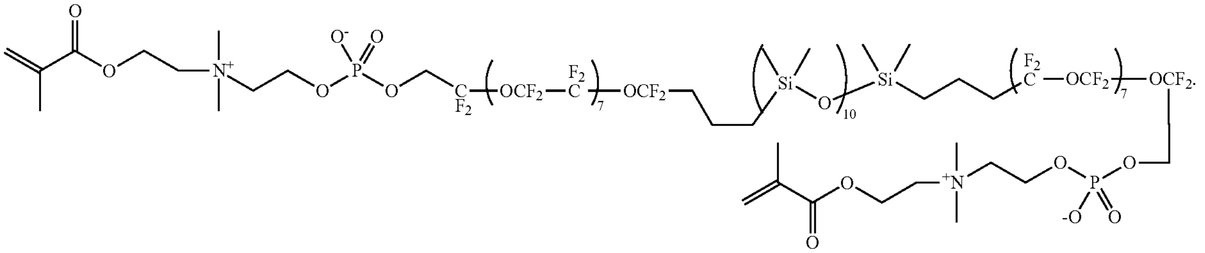

A polymerizable compound of the present invention may have the formula (III)

(III)

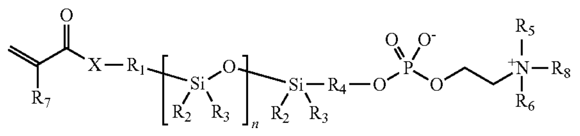

wherein: $R_1$ is an alkylene or polyether linking group of linear or branched low molecular weight or oligomeric structure having up to 10 carbon atoms; $R_2$ and $R_3$ are the same or different groups selected from alkyl, trialkylsiloxy, substituted silicone, alkoxy, alicyclic, and aromatic groups; n is a number of repeat silicone units from 1 to 700 units; $R_4$ is an alkylene, polyether, perfluorinated polyether, carbamate, ester, amide, or urea linkage having up to 30 linking atoms; $R_5$ and $R_6$ are the same or different alkyl, alkoxy, or aromatic groups or alicyclic rings containing 3 to 6 carbon atoms; $R_7$ is H or an alkyl group containing 1 to 6 carbon atoms; $R_8$ is an alkyl or alkoxy group containing 1 to 22 carbon atoms; and X is O, NH, or N—$C_{1-6}$alkyl.

A specific example thereof includes compound 3:

A polymerizable compound of the present invention may have the formula (IV)

(IV)

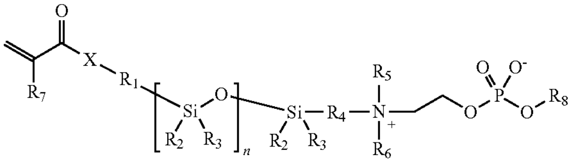

wherein: $R_1$ is an alkylene or polyether linking group of linear or branched low molecular weight or oligomeric structure having up to 10 carbon atoms; $R_2$ and $R_3$ are the same or different groups selected from alkyl, trialkylsiloxy, substituted silicone, alkoxy, alicyclic, and aromatic groups; n is a number of repeat silicone units from 1 to 700 units; $R_4$ is an alkylene, polyether, perfluorinated polyether, carbamate, ester, amide, or urea linkage having up to 30 linking atoms; $R_5$ and $R_6$ are the same or different alkyl, alkoxy, or aromatic groups or alicyclic rings containing 3 to 6 carbon atoms; $R_7$ is H or an alkyl group containing 1 to 6 carbon atoms; $R_8$ is an alkyl or alkoxy group containing 1 to 22 carbon atoms; and X is O, NH, or N—$C_{1-6}$alkyl.

3

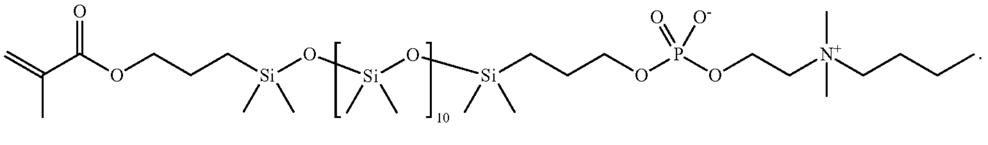

A specific example thereof includes compound 5:

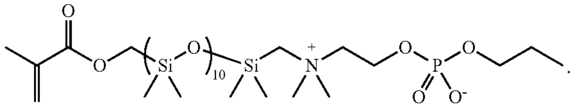

lene, polyether, or perfluorinated polyether linkage having up to 30 carbon and/or oxygen linking atoms; $R_5$ and $R_6$ are the same or different alkyl, alkoxy, or aromatic groups or alicyclic rings containing 3 to 6 carbon atoms—preferably alkyl, alkoxy, or aromatic groups, more preferably methyl, n-butyl, methoxy, ethoxy, isopropoxy, or phenyl groups; and $R_7$ is an alkyl or alkoxy group containing 1 to 22 carbon atoms—preferably an alkyl group, more preferably $C_{1-6}$alkyl.

Specific examples of such compounds are

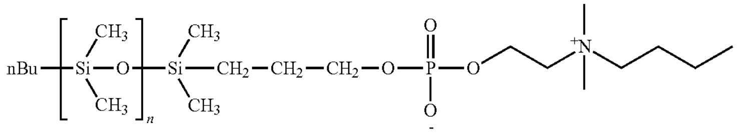

and

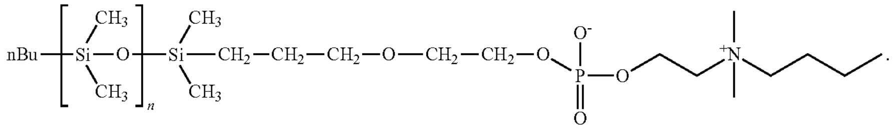

This invention also contemplates a polymer formed by polymerizing any one of the foregoing monomers, or by polymerizing a formulation containing any one of the foregoing monomers. Such polymerization may be initiated by a free radical polymerization initiator in the presence of heat, ultraviolet light, visible light, or another source of radiation. The polymerization initiator may be selected from the group consisting of acetal peroxide, lauroyl peroxide, decanoyl peroxide, stearoyl peroxide, benzoyl peroxide, tert-butyl peroxypivalate, and peroxydicarbonate.

A non-polymerizable compound of the present invention may have the formula (V)

(V)

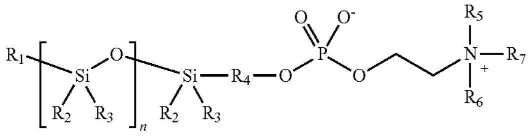

wherein: $R_1$ is an alkyl or alkoxy group of linear, branched, or cyclic structure, or an aromatic group, having up to 20 carbon atoms—preferably an alkyl group or a monocyclic aromatic hydrocarbon group, more preferably methyl, n-butyl, methoxy, or phenyl; $R_2$ and $R_3$ are the same or different groups selected from alkyl, trialkylsiloxy, substituted silicone, alkoxy, alicyclic, and aromatic groups—preferably alkyl, alkoxy, and aromatic groups, more preferably methyl, n-butyl, methoxy, ethoxy, isopropoxy, or phenyl groups; n is a number of repeat silicone units from 1 to 20,000 units—preferably from 1 to 700, more preferably from 1 to 15 units; $R_4$ is an alkylene or polyether or perfluorinated polyether linkage having up to 30 linking atoms—preferably an alky- A non-polymerizable compound of the present invention may have the formula (VI)

(VI)

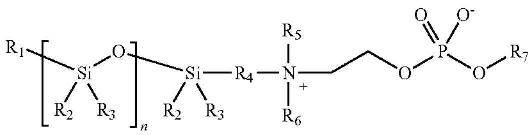

wherein: $R_1$ is an alkyl or alkoxy group of linear, branched, or cyclic structure, or an aromatic group, having up to 20 carbon atoms—preferably an alkyl group or a monocyclic aromatic hydrocarbon group, more preferably methyl, n-butyl, methoxy, or phenyl; $R_2$ and $R_3$ are the same or different groups selected from alkyl, trialkylsiloxy, substituted silicone, alkoxy, alicyclic, and aromatic groups—preferably alkyl, alkoxy, and aromatic groups, more preferably methyl, n-butyl, methoxy, ethoxy, isopropoxy, or phenyl groups; n is a number of repeat silicone units from 1 to 20,000 units—preferably from 1 to 700 units, more preferably from 1 to 15 units; $R_4$ is an alkylene or polyether or perfluorinated polyether linkage having up to 30 linking atoms—preferably an alkylene, polyether, or perfluorinated polyether linkage having up to 30 carbon and/or oxygen linking atoms; $R_5$ and $R_6$ are the same or different alkyl, alkoxy, or aromatic groups or alicyclic rings containing 3 to 6 carbon atoms—preferably alkyl, alkoxy, or aromatic groups, more preferably methyl, n-butyl, methoxy, ethoxy, isopropoxy, or phenyl groups; and $R_7$ is an alkyl or alkoxy group containing 1 to 22 carbon atoms—preferably an alkyl group, more preferably $C_{1-6}$alkyl.

A non-polymerizable compound of the present invention may have the formula (VII) or (VIII)

(VII)

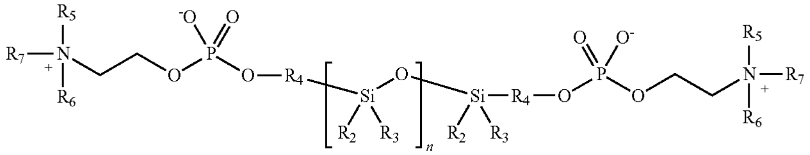

(VIII)

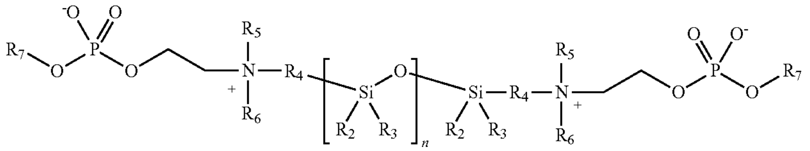

in which $R_2$ and $R_3$ are the same or different groups selected from alkyl, trialkylsiloxy, substituted silicone, alkoxy, alicyclic, and aromatic groups—preferably alkyl, alkoxy, and aromatic groups, more preferably methyl, n-butyl, methoxy, ethoxy, isopropoxy, or phenyl groups; n is a number of repeat silicone units from 1 to 20,000 units—preferably from 1 to 700 units, more preferably from 1 to 15 units; $R_4$ is an alkylene or polyether or perfluorinated polyether linkage having up to 30 linking atoms—preferably an alkylene, polyether, or perfluorinated polyether linkage having up to 30 carbon and/or oxygen linking atoms; $R_5$ and $R_6$ are the same or different alkyl, alkoxy, or aromatic groups or alicyclic rings containing 3 to 6 carbon atoms—preferably alkyl, alkoxy, or aromatic groups, more preferably methyl, n-butyl, methoxy, ethoxy, isopropoxy, or phenyl groups; and $R_7$ is an alkyl or alkoxy group containing 1 to 22 carbon atoms—preferably an alkyl group, more preferably $C_{1-6}$alkyl.

The present invention includes an ophthalmic lens having an antifouling surface comprising a polymer made from a formulation containing a monomer compound of the invention as described herein, or a polymer made from such monomers, and/or a non-polymerizable compound of the invention as described herein. To manufacture such an ophthalmic lens, a monomer mixture comprising a polymerizable silicone compound of the invention, a colorant, a reactive diluent, a toughening agent, a UV-absorbing agent, a free radical polymerization initiator, and a compatibilizing solvent may be cured to a cast shape by free radical polymerization. Alternatively, a monomer mixture comprising a polymerizable silicone compound other than those described herein, a non-polymerizable zwitterionic silicone compound of the invention, a colorant, a toughening agent, a UV-absorbing agent, a free radical polymerization initiator, and a reactive diluent may be cured to a cast shape by free radical polymerization.

Also contemplated by this invention are an ophthalmic lens care solution and an ophthalmic lens packaging solution, both comprising a non-polymerizable zwitterionic phosphorylcholine-group-containing silicone compound of the invention.

This invention contemplates further a breathable wound dressing comprising a polymer made from a monomer compound of as described herein, a polymer as described herein made from such monomer, and/or a non-polymerizable zwitterionic silicone compound as described herein.

Yet another embodiment of the present invention is a medical device—for instance, a coronary stent or a vascular stent—having a non-thrombogenic surface, wherein the surface comprises a polymer made from a polymerizable silicone compound comprising a zwitterionic phosphorylcholine group and at least one vinyl endgroup as disclosed herein.

Examples of the Invention

Illustrative specific examples of polymerizable compounds having one or more zwitterionic phosphorylcholine moieties in accordance with the present invention include the following:

1

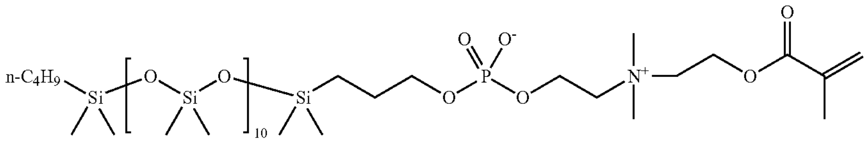

2

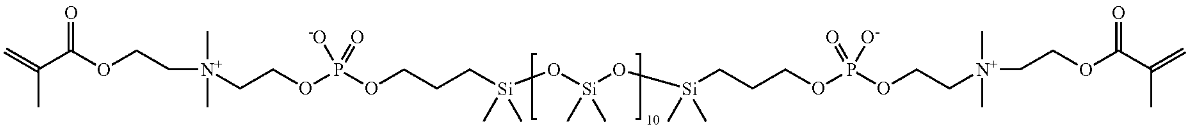

3

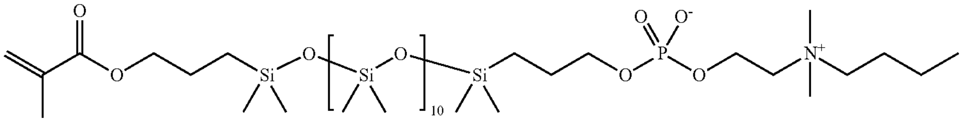

-continued

4

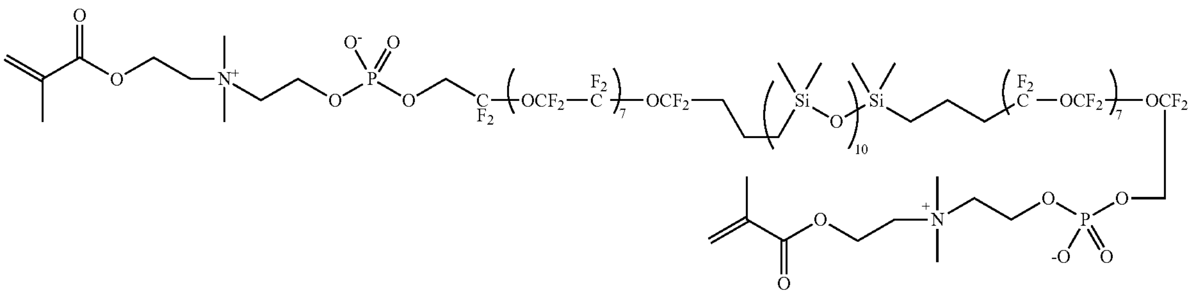

5

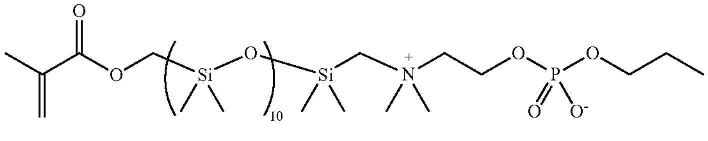

While compound 4 above shows a fluorinated polyethylene oxide block, since incorporation of fluorine atom can dramatically increase oxygen permeability (Dk) due to very high solubility of oxygen in fluorine-containing materials, the fluorinated polyether block need not be limited to fluorinated polyethylene oxides only, and can encompass other fluorinated polyethers.

Illustrative specific examples of non-polymerizable compounds having zwitterionic phosphorylcholine moieties in accordance with the present invention include the following:

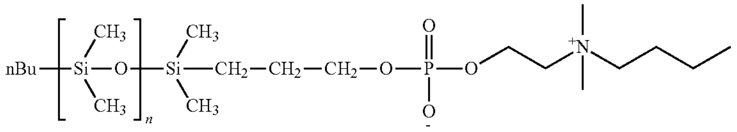

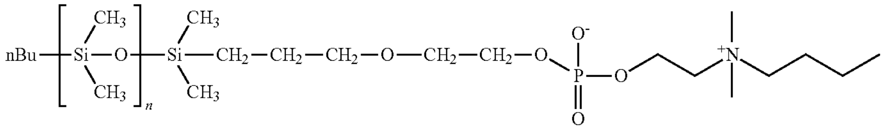

These and other compounds of the present invention can be synthesized from commercially available silicones and other components using methods known in general to those skilled in the art. For instance, a silicone terminated with an aliphatic hydroxyl group can be reacted with 2-chloro-2-oxo-1,3,2-dioxaphospholane in the presence of an alkaline material to split off the hydrogen atom from the hydroxyl group and the chloro atom from the 2-chloro-2-oxo-1,3,2-dioxaphospholane group, forming an intermediate in which a 2-oxo-1,3,2-dioxaphospholane moiety is linked through the aliphatic linkage to the silicone moiety. Then the intermediate is reacted with an aliphatic amine. To make the compounds of formulas 1 and 2, for instance, the aliphatic amine would be dimethylaminoethyl methacrylate, and the resulting reaction product would contain a vinyl group (from the methacrylate) attached to the resulting ammonium portion of the zwitterionic compound. See Synthetic Example 1 below. To make the compound of formula 3, n-butyldimethylamine would be used, and the vinyl group would be attached in another step to a portion of the molecule remote from the zwitterionic moiety. To make a non-polymerizable silicone compound comprising a zwitterionic phosphorylcholine group in accordance with the present invention, no vinyl group would be introduced into the molecule, as illustrated in Synthetic Examples 2 and 3. The foregoing approach provides silicone compounds comprising a zwitterionic phosphorylcholine group in which the phosphorylcholine anion is closer to the silicone moiety than is the ammonium cation. As illustrated in the compound of formula 5, the present invention also provides silicone compounds comprising a zwitterionic phosphorylcholine group in which the ammonium cation is closer to the silicone moiety than is the phosphorylcholine anion. These variants of the compounds of the invention can be made by judicious selection of the appropriate reactants and order of reaction steps. That is, one would first join the amine to the silicone moiety, and would then react the resulting intermediate with an alkyl substituted 2-oxo-1,3,2-dioxaphospholane compound.

The monofunctional and difunctional reactive monomers and macromers can be polymerized by free radical, ionic, organometallic, or group transfer mechanisms with suitable catalysts or initiators (which can be induced with or without the presence of heat or a source of radiation) known to persons skilled in the art.

Illustrative Synthetic Examples follow.

Synthetic Examples

Synthetic Example 1

Synthesis of a polymerizable silicone compound containing two polymerizable phosphorylcholine moieties. This compound is of the type illustrated by compound 2 above.

Step 1:

Into a 4-neck 250-mL round bottom flask, 38.15 g carbinol-terminated PDMS (DMS-C16 obtained from GELEST), 7.92 g triethylamine and 100 mL anhydrous THF were added. The mixture was cooled down to below −20° C. A solution of 2-chloro-2-oxo-1,3,2-dioxaphospholane (COP) 10.96 g in 50 mL anhydrous THF was then added dropwise into the flask while maintaining the mixture temperature below −20° C. The reaction was continued for 3 hours below −20° C., and then slowly warmed to room temperature. The salt by-product was filtered off, and the solvent removed under reduced pressure to yield the bis-oxo-dioxaphospholane silicone intermediate.

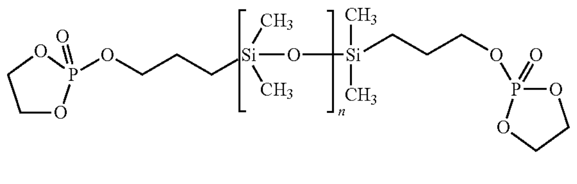

Step 2:

A mixture of 20 g of the bis-oxo-dioxaphospholane silicone intermediate from Step 1 was mixed with 2.60 g anhydrous dimethylaminoethyl methacrylate and 40 ml anhydrous acetonitrile in a two neck RBF equipped with condenser and $N_2$ sparge. The reaction mixture was heated in a sealed container for 24 hours. After the reaction, acetonitrile was removed by rotovap and the product crude was washed repeatedly with cyclohexane. Removal of cyclohexane yielded the polymerizable di functionalized PC containing silicone. The structural purity of the compound was confirmed by spectroscopic methods.

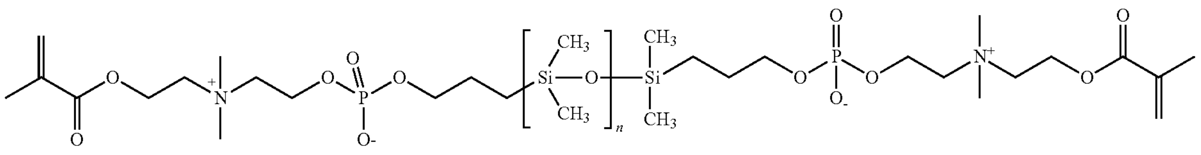

Synthetic Example 2

Synthesis of a Non-Polymerizable Silicone Composition Containing a Phosphorylcholine Moiety Step 1: Synthesis of Hydroxypropyl-nBuPDMS (HPnBuPDMS)

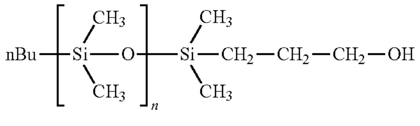

35.10 g allyl alcohol and 65 g of anhydrous hexanes was charged into a 500 ml round bottom flask equipped with magnetic stir bar, thermocouple thermometer, water condenser, and addition funnel 0.16 g of Platinum(0)-1,3-divinyl-1,1,3,3-tetramethyldisiloxane (Karstedt catalyst) complex in xylenes (~2 wt % Pt) was added to the reaction medium. The mixture was stirred to yield a homogeneous solution. 123.60 g n-Butyl polydimethylsiloxane hydride obtained commercially from GELEST was added drop-wise to the allyl alcohol solution at 60° C. over a period of 45 minutes. The reaction was left overnight (~18 h) and quenched with diethyleneethylenediamine. The crude reaction mixture in hexanes was extracted with 2:1 methanol: water (v/v) mixture until all allyl alcohol was removed. The raffinate was dried over anhydrous sodium sulfate and the hexanes was removed by rotovap at 35° C. under reduced pressures to yield the product as a colorless oil. The structural purity of the product (HPnBuPDMS) was confirmed by $^1H$ NMR.

Step 2: Synthesis of mPDMSOP

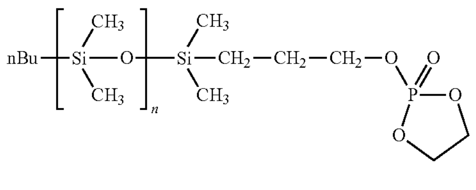

111.44 g of HPnBuPDMS (from Step 1), 14.91 g triethylamine, and 50 ml of anhydrous tetrahydrofuran (THF) solvent was charged into a 500 ml three neck RBF equipped with a magnetic stir bar, Nitrogen inlet and outlet and addition funnel. The reaction mix was cooled to −20° C. under a blanket of $N_2$ and 15 g of 2-chloro-2-oxo-1,3,2-dioxaphosphorane (COP) dissolved in 75 g of anhydrous THF was added dropwise from the addition funnel. After the complete addition of the COP solution, the reaction mix was stirred at −10° C. for 6 hours. The turbid reaction mix was filtered to remove the triethylamine hydrochloride precipitate and the filtrate evaporated in vacuo to yield the oxo-dioxaphospholane silicone intermediate, mPDMSOP.

Step 3: Synthesis of mPDMSPC

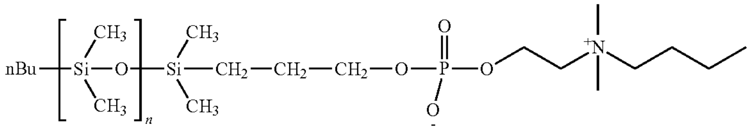

20 g of mPDMSOP (from Step 2) and 2.05 g of n-butyldimethylamine were dissolved in dry acetonitrile and allowed to react under $N_2$ atmosphere at 65° C. for 24 hours. After the reaction, acetonitrile was removed by rotovap and the product crude was washed repeatedly with cyclohexane. The resulting product was dried under vacuo to yield the PC substituted silicone (mPDMSPC). The structural purity of the product was confirmed by spectroscopic methods.

Synthetic Example 3

Synthesis of a Non-Polymerizable Silicone Composition Containing a Phosphorylcholine Moiety and Ether Groups Step 1: Synthesis of Hydroxyethyloxypropyl-nBuPDMS (HEPnBuPDMS)

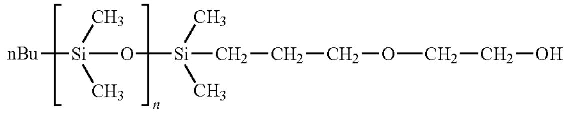

61.28 g 2-allyloxyethanol and 65 g of anhydrous hexanes was charged into a 500 ml round bottom flask equipped with magnetic stir bar, thermocouple thermometer, water condenser, and addition funnel. 0.16 g of Platinum(0)-1,3-divinyl-1,1,3,3-tetramethyldisiloxane (Karstedt catalyst) complex in xylenes (~2 wt % Pt) was added to the reaction medium. The mixture was stirred to yield a homogeneous solution. 123.60 g n-Butyl polydimethylsiloxane hydride (nBuPDMSH) obtained commercially from GELEST was added drop-wise to the 2-allyloxyethanol solution at 60° C. over a period of 45 minutes. The reaction was left overnight (~18 h) and quenched with diethyleneethylenediamine. The crude reaction mixture in hexanes was extracted with 2:1 methanol:water (v/v) mixture until all allyl alcohol was removed. The raffinate was dried over anhydrous sodium sulfate and the hexanes was removed by rotovap at 35° C. under reduced pressures to yield >90% of the product as a colorless oil. The structural purity of the product was confirmed by $^1H$ NMR.

Step 2: Synthesis of mPDMSEPOP

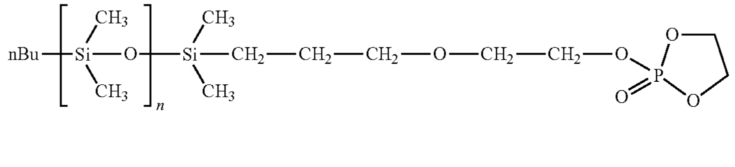

117 g of HEPnBuPDMS (from Step 1), 14.91 g triethylamine and 50 ml of anhydrous tetrahydrofuran (THF) solvent was charged into a 500 ml three neck RBF equipped with a magnetic stir bar, Nitrogen inlet and outlet and addition funnel. The reaction mix was cooled to −20° C. under a blanket of $N_2$ and 15 g of 2-chloro-2-oxo-1,3,2-dioxaphosphorane (COP) dissolved in 75 g of anhydrous THF was added dropwise from the addition funnel. After the complete addition of the COP solution, the reaction mix was stirred at −10° C. for 6 hours. The turbid reaction mix was filtered to remove the triethylamine hydrochloride precipitate and the filtrate evaporated in vacuo to yield the oxo-dioxaphospholane silicone intermediate, mPDMSEPOP.

Step 3: Synthesis of mPDMSPC

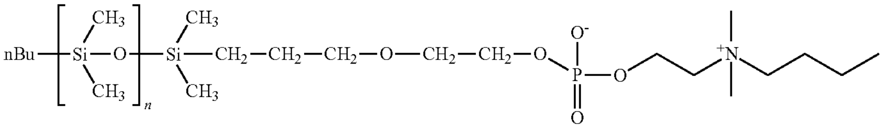

20 g of mPDMSEOP (from Step 2) and 1.96 g of n-butyldimethylamine were dissolved in dry acetonitrile and allowed to react under $N_2$ atmosphere at 65° C. After the reaction, acetonitrile was removed by rotovap and the product crude was washed repeatedly with cyclohexane. The structural purity of the compound (mPDMSOP) was confirmed by 1H NMR. The resulting product was dried under vacuo to yield the PC substituted silicone (mPDMSPC). The structural purity of the product was confirmed by spectroscopic methods.

Using the Compounds

The present invention provides two types of compounds: polymerizable silicone compounds comprising a zwitterionic phosphorylcholine group and at least one vinyl group, and non-polymerizable silicone compounds comprising a zwitterionic phosphorylcholine group. The polymerizable silicone compounds comprising a zwitterionic phosphorylcholine group and at least one vinyl group can be used as polymerizable components for medical devices, as polymerizable components in formulations for the manufacture of ophthalmic lenses. Both types of silicone compounds comprising a zwitterionic phosphorylcholine group provided by the present invention can be used as components in ophthalmic lens formulations, as components for the post-treatment of ophthalmic lenses, as components in ophthalmic lens packaging solutions, as additives in ophthalmic lens care solutions, as coating layers for surface modification of medical devices by means of plasma or glow discharge, as active components in tissue adhesion barriers, as active components in liquid adhesive formulations, as active components in formulations for catheter coatings, as active components in breathable wound dressings, and in medical devices to impart antithrombogenic and/or antifouling properties. Persons skilled in the art will readily appreciate the manner in which the presently claimed novel compounds can be utilized in such applications. For the sake of illustration, however, more detail on some of these utilities is provided below.

OPHTHALMIC LENSES: The polymerizable and non-polymerizable zwitterionic phosphorylcholine-containing silicones described herein can be used as active components in a contact lens monomer formulation to yield silicone hydrogel lenses with very low protein deposits as well as reduced lipid depositions. These advantages are believed to result from the hydrophilic nature of the surfaces of lenses made from formulations that incorporate the present compounds. The polymerizable monomers disclosed herein, when used in a lens formulation, will present a covalently bound antifouling surface—due to the fact that the ionic zwitterionic phosphorylcholine portion of the molecule will migrate to the surface in a moist environment in preference to the hydrophobic silicone portion of the molecule.

For lens applications in accordance with the present invention, the monomer mixtures employed will include a polymerizable material of this invention mixed with various conventional lens-forming monomers and compounds. All the lens-forming monomers will normally be monomers that are polymerizable by free radical polymerization, usually an activated unsaturated radical, and most preferably an ethylenically unsaturated (vinyl) radical. The conventional lens-forming monomers may be low molecular weight compounds that are polymerizable by free radical polymerization, or may be higher molecular weight compounds also referred to as prepolymers or macromonomers. Optionally, the initial monomeric mixture may also include additional materials such as solvents, colorants, toughening agents, UV-absorbing agents, and other materials known in the contact lens art. Representative solvents are disclosed in U.S. Pat. No. 5,260,000 (Nandu et al.) and U.S. Pat. No. 6,020,445 (Vanderlaan et al.).

The instant copolymers can be readily cured to cast shapes by conventional free radical polymerization methods, where the monomeric mixture is exposed to light radiation, such as visible light or UV radiation, to heat, or to both, in order to induce polymerization. Representative free radical thermal polymerization initiators are organic peroxides, such as acetal peroxide, lauroyl peroxide, decanoyl peroxide, stearoyl peroxide, benzoyl peroxide, tert-butyl peroxypivalate, peroxydicarbonate, and the like, employed in a concentration of about 0.01 to 1 percent by weight of the total monomer mixture. Representative UV initiators are those known in the field such as, benzoin methyl ether and benzoin ethyl ether.

Persons skilled in the art are well aware of how to make silicone hydrogel contact lenses in general. See, e.g., U.S. Pat. No. 4,600,751 (Lee et al.); U.S. Pat. No. 7,268,198 (Kunzler et al.); and U.S. Pat. No. 7,540,609 B2 (Chen et al.). Based upon the present disclosure, persons skilled in the art will readily understand how to make silicone hydrogel contact lenses incorporating the novel zwitterionic phosphorylcholine-containing silicone compounds disclosed herein.

The non-polymerizable zwitterionic phosphorylcholine-containing silicone monomers disclosed herein act as a medium to support an interconnected polymer network (IPN) with other, polymerizable lens components after curing steps in the manufacturing process. A high molecular weight non-polymerizable PC-containing silicone may be added in the formulation to support IPN structures. High molecular weight non-polymerizable zwitterionic phosphorylcholine-containing silicones may be used to reduce the presence of leachables after manufacture and during wear of the contact lens. In another embodiment, both the polymerizable and non-polymerizable zwitterionic phosphorylcholine-containing silicones may be employed in the contact lens formulation.

The polymerizable silicones disclosed herein can also be incorporated as a post treatment step to form a zwitterionic phosphorylcholine-containing silicone surface coating on the contact lens. In this process the contact lens is treated with a solution containing zwitterionic phosphorylcholine-containing silicone monomer followed by polymerization in the presence of suitable radical initiator to yield the said coating. The non-polymerizable zwitterionic phosphorylcholine-containing silicone monomers will also find utility in the lens packaging solution during the manufacturing process to support inclusion of the phosphorylcholine-linked silicones into the contact lens matrix. This can be achieved by agitation, ultrasonication, or by application of an energy source such as heat, steam, thermal, or other source of radiation. Alternatively, the incorporation of the non-polymerizable zwitterionic phosphorylcholine-containing silicones into the contact lens can be achieved during the sterilization step of the manufacturing process.

OPHTHALMIC LENS CARE SOLUTION: The non-polymerizable zwitterionic phosphorylcholine-containing silicones can be used as compatibilizing components in contact lens care solutions for imparting surface wettability/lubricity to silicone hydrogel contact lenses. The non-polymerizable zwitterionic phosphorylcholine-containing compounds can be used to complement antimicrobial components and other components present in lens care formulations. Combination of both biofouling and antimicrobial properties provided by the compounds of the present invention enables highly effective lens care solutions for cleaning and disinfecting contact lenses.

BREATHABLE WOUND DRESSINGS: The zwitterionic phosphorylcholine-containing silicones can be similarly incorporated into formulations to prepare breathable film constructs for use as wound bed contacting layers or as absorbent dressings for exudating wounds. The non-polymerizable zwitterionic phosphorylcholine-containing silicone monomers disclosed herein, on the other hand, can act as a medium to support an interconnected polymer network (IPN) with polymerizable wound dressing components after curing steps in the manufacturing process. High molecular weight (50,000 to 1,500,000 Daltons weight average molecular weight) non-polymerizable zwitterionic phosphorylcholine-containing silicones may be used to reduce the presence of leachables after manufacture and during wear of the contact lens. In yet another embodiment, both the polymerizable and non-polymerizable zwitterionic phosphorylcholine-containing silicones may be added in the contact lens formulation.

Sheets and other shapes of foamed polymer constructs with small, open cells capable of holding fluids can be manufactured by methods known to those skilled in the art. The phosphorylcholine-enriched surface on the polymer constructs will act as a bacterial barrier, while the silicone component will allow flow of oxygen to promote faster wound healing.

ANTI-THROMBOGENIC APPLICATIONS: Polymers made from the polymerizable silicone compounds of the present invention provide anti-thrombogenic surfaces with reduced platelet adhesion and activations. As such, they are suitable for use in medical devices which contact blood, such as coronary and vascular stents. Persons skilled in the art are familiar with the use of polymeric systems to make or coat such medical devices. See, for instance, U.S. Pat. No. 5,837,313 (Drug Release Stent Coating Process); U.S. Pat. No. 6,099,563 (Substrates, Particularly Medical Devices, Provided with Bio-Active/Biocompatible Coatings); U.S. Pat. No. 6,248,127 B1 (Thromboresistant Coated Medical Device); and U.S. Pat. No. 6,517,889 B1 (Process for Coating a Surface of a Stent). The following publications also provide general guidance for the use of phosphorylcholine compounds in imparting anti-thrombogenic properties. Yoneyama, et al, "The vascular prosthesis without pseudointima prepared by antithrombogenic phospholipid polymer," *Biomaterials* 23:1455-1459 (2002); Ishihara, et al., "Reduced thrombogenicity of polymers having phospholipid polar groups," *J. Biomed. Mater. Res.,* 24:1069-1077 (1990); Xu, et al., "Ozone-induced grafting phosphorylcholine polymer onto silicone film to improve hemocompatibility," *Colloids and Surfaces B: Biointerfaces,* 30:215-223 (2003). The novel zwitterionic compounds of the present invention may be used to make medical devices in manners similar to those described for previously known compounds, including phosphorylcholine compounds.

Specific exemplary embodiments of the present invention have been shown and described in the foregoing specification. It will be appreciated by those skilled in the art, however, that variations may be made to the illustrative embodiments without departing from the principles and spirit of the present invention.

What is claimed is:

1. A polymerizable silicone compound comprising a silicone moiety having a weight average molecular weight of from 500 to 50,000 Daltons, wherein said polymerizable silicone compound is selected from the group consisting of compounds having the formula (I)

(I)

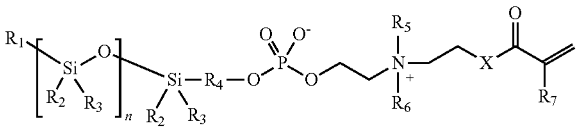

wherein:

$R_1$ is an alkyl or alkoxy group of linear, branched, or cyclic structure, or an aromatic group, having up to 20 carbon atoms;

$R_2$ and $R_3$ are the same or different groups selected from alkyl, trialkylsiloxy, silicone, alkoxy, alicyclic, and aromatic groups;

n is a number of repeat silicone units from 1 to 700 units;

$R_4$ is an alkylene, polyether, perfluorinated polyether, carbamate, ester, amide, or urea linkage having up to 30 linking atoms;

$R_5$ and $R_6$ are the same or different alkyl, alkoxy, or aromatic groups or alicyclic rings containing 3 to 6 carbon atoms;

$R_7$ is H or an alkyl group containing 1 to 6 carbon atoms; and

X is O, NH, or N—$C_{1-6}$alkyl, compounds having the formula (II)

(II)

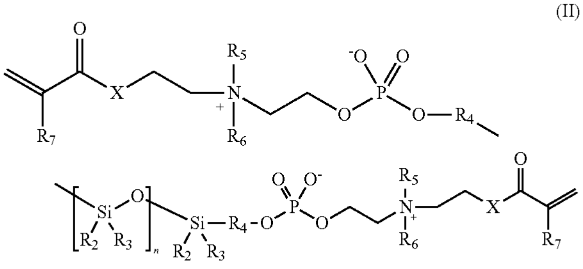

wherein:

$R_2$ and $R_3$ are the same or different groups selected from alkyl, trialkylsiloxy, silicone, alkoxy, alicyclic, and aromatic groups;

n is a number of repeat silicone units from 1 to 700 units;

$R_4$ is an alkylene, polyether, perfluorinated polyether, carbamate, ester, amide, or urea linkage having up to 30 linking atoms;

$R_5$ and $R_6$ are the same or different alkyl, alkoxy, or aromatic groups or alicyclic rings containing 3 to 6 carbon atoms;

$R_7$ is H or an alkyl group containing 1 to 6 carbon atoms; and

X is O, NH, or N—$C_{1-6}$alkyl, compounds having the formula (III)

(III)

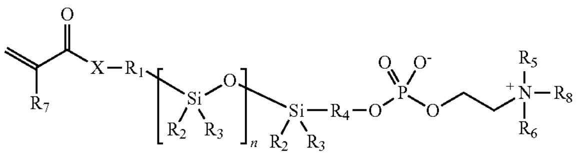

wherein:

$R_1$ is an alkylene or polyether linking group of linear or branched low molecular weight or oligomeric structure having up to 10 carbon atoms;

$R_2$ and $R_3$ are the same or different groups selected from alkyl, trialkylsiloxy, silicone, alkoxy, alicyclic, and aromatic groups;

n is a number of repeat silicone units from 1 to 700 units;

$R_4$ is an alkylene, polyether, perfluorinated polyether, carbamate, ester, amide, or urea linkage having up to 30 linking atoms;

$R_5$ and $R_6$ are the same or different alkyl, alkoxy, or aromatic groups or alicyclic rings containing 3 to 6 carbon atoms;

$R_7$ is H or an alkyl group containing 1 to 6 carbon atoms;

$R_8$ is an alkyl or alkoxy group containing 1 to 22 carbon atoms; and

X is O, NH, or N—$C_{1-6}$alkyl, and compounds having the formula (IV)

(IV)

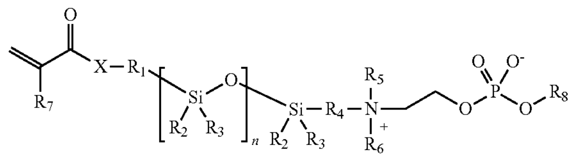

wherein:

$R_1$ is an alkylene or polyether linking group of linear or branched low molecular weight or oligomeric structure having up to 10 carbon atoms;

$R_2$ and $R_3$ are the same or different groups selected from alkyl, trialkylsiloxy, silicone, alkoxy, alicyclic, and aromatic groups;

n is a number of repeat silicone units from 1 to 700 units;

$R_4$ is an alkylene, polyether, perfluorinated polyether, carbamate, ester, amide, or urea linkage having up to 30 linking atoms;

$R_5$ and $R_6$ are the same or different alkyl, alkoxy, or aromatic groups or alicyclic rings containing 3 to 6 carbon atoms;

$R_7$ is H or an alkyl group containing 1 to 6 carbon atoms;

$R_8$ is an alkyl or alkoxy group containing 1 to 22 carbon atoms; and

X is O, NH, or N—$C_{1-6}$alkyl.

2. The compound of claim 1, having the structure 1

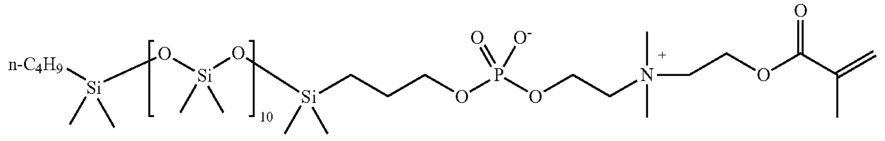

1 or the structure 2

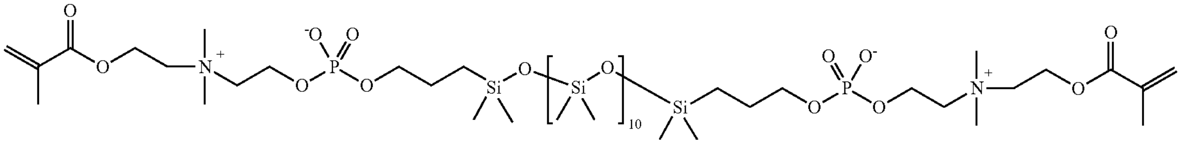

2 or the structure 4

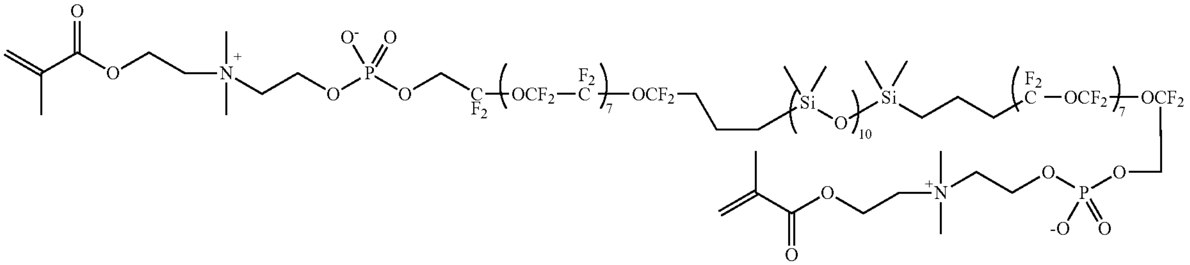

4 or the structure 3

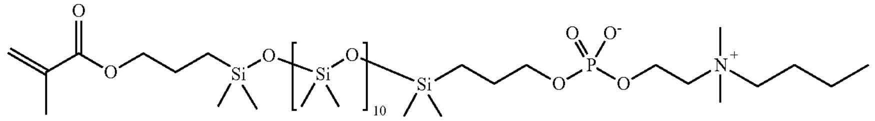

3 or the structure 5

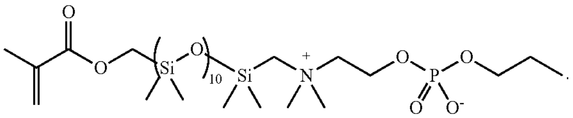

5

3. A polymer formed by polymerizing a compound of claim 1 or a formulation containing a compound of claim 1, wherein said polymerization is initiated by a free radical polymerization initiator in the presence of heat, ultraviolet light, visible light, or another source of radiation.

4. An ophthalmic lens having an antifouling surface comprising a polymer of claim 3.

5. A breathable wound dressing comprising a polymer of claim 3.

6. A medical device configured as a coronary or vascular stent, having a non-thrombogenic surface, said surface comprising a polymer made from a monomer compound of claim 1.

7. An ophthalmic lens comprising a polymer of claim 3.

8. The ophthalmic lens of claim 7, wherein a formulation comprising said compound, and further comprising a colorant, a reactive diluent, a toughening agent, a UV-absorbing agent, a free radical polymerization initiator, and a compatibilizing solvent is cured to a cast shape by free radical polymerization.

9. The ophthalmic lens of claim 7, wherein a formulation comprising said compound, and further comprising a colorant, a toughening agent, a UV-absorbing agent, a free radical polymerization initiator, and a reactive diluent, is cured to a cast shape by free radical polymerization.

10. An ophthalmic lens having an antifouling surface comprising a silicone compound comprising a silicone moiety having a weight average molecular weight of from 1000 to 1,500,000 Daltons, wherein said silicone compound is selected from the group consisting of compounds having the formula (V)

(V)

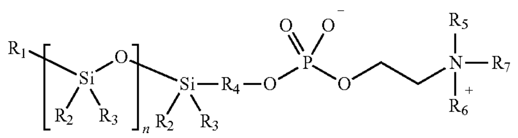

wherein:

$R_1$ is an alkyl or alkoxy group of linear, branched, or cyclic structure, or an aromatic group, having up to 20 carbon atoms;

$R_2$ and $R_3$ are the same or different groups selected from alkyl, trialkylsiloxy, silicone, alkoxy, alicyclic, and aromatic groups;

n is a number of repeat silicone units from 1 to 20,000 units;

$R_4$ is an alkylene or polyether or perfluorinated polyether linkage having up to 30 linking atoms;

$R_5$ and $R_6$ are the same or different alkyl, alkoxy, or aromatic groups or alicyclic rings containing 3 to 6 carbon atoms; and $R_7$ is an alkyl or alkoxy group containing 1 to 22 carbon atoms, compounds having the formula (VI)

(VI)

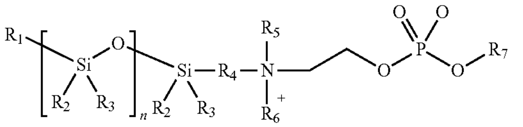

wherein:

$R_1$ is an alkyl or alkoxy group of linear, branched, or cyclic structure, or an aromatic group, having up to 20 carbon atoms;

$R_2$ and $R_3$ are the same or different groups selected from alkyl, trialkylsiloxy, silicone, alkoxy, alicyclic, and aromatic groups;

n is a number of repeat silicone units from 1 to 20,000 units;

$R_4$ is an alkylene or polyether or perfluorinated polyether linkage having up to 30 linking atoms;

$R_5$ and $R_6$ are the same or different alkyl, alkoxy, or aromatic groups or alicyclic rings containing 3 to 6 carbon atoms; and $R_7$ is an alkyl or alkoxy group containing 1 to 22 carbon atoms, and compounds having the formula (VII)

(VII)

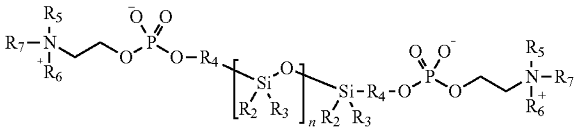

or the formula (VIII)

(VIII)

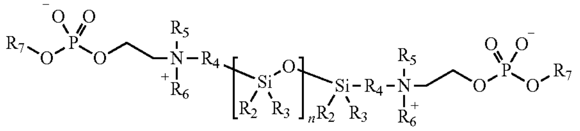

wherein:

$R_2$ and $R_3$ are the same or different groups selected from alkyl, trialkylsiloxy, silicone, alkoxy, alicyclic, and aromatic groups;

n is a number of repeat silicone units from 1 to 20,000 units;

$R_4$ is an alkylene or polyether or perfluorinated polyether linkage having up to 30 linking atoms;

$R_5$ and $R_6$ are the same or different alkyl, alkoxy, or aromatic groups or alicyclic rings containing 3 to 6 carbon atoms; and $R_7$ is an alkyl or alkoxy group containing 1 to 22 carbon atoms.

11. A breathable wound dressing comprising a silicone compound comprising a silicone moiety having a weight average molecular weight of from 1000 to 1,500,000 Daltons, wherein said silicone compound is selected from the group consisting of compounds having the formula (V)

(V)

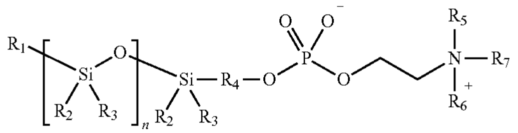

wherein:

$R_1$ is an alkyl or alkoxy group of linear, branched, or cyclic structure, or an aromatic group, having up to 20 carbon atoms;

$R_2$ and $R_3$ are the same or different groups selected from alkyl, trialkylsiloxy, silicone, alkoxy, alicyclic, and aromatic groups;

n is a number of repeat silicone units from 1 to 20,000 units;

$R_4$ is an alkylene or polyether or perfluorinated polyether linkage having up to 30 linking atoms;

$R_5$ and $R_6$ are the same or different alkyl, alkoxy, or aromatic groups or alicyclic rings containing 3 to 6 carbon atoms; and $R_7$ is an alkyl or alkoxy group containing 1 to 22 carbon atoms, compounds having the formula (VI)

(VI)

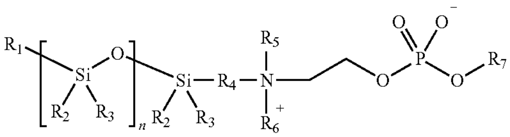

wherein:

$R_1$ is an alkyl or alkoxy group of linear, branched, or cyclic structure, or an aromatic group, having up to 20 carbon atoms;

$R_2$ and $R_3$ are the same or different groups selected from alkyl, trialkylsiloxy, silicone, alkoxy, alicyclic, and aromatic groups;

n is a number of repeat silicone units from 1 to 20,000 units;

$R_4$ is an alkylene or polyether or perfluorinated polyether linkage having up to 30 linking atoms;

$R_5$ and $R_6$ are the same or different alkyl, alkoxy, or aromatic groups or alicyclic rings containing 3 to 6 carbon atoms; and $R_7$ is an alkyl or alkoxy group containing 1 to 22 carbon atoms, and compounds having the formula (VII)

(VII)

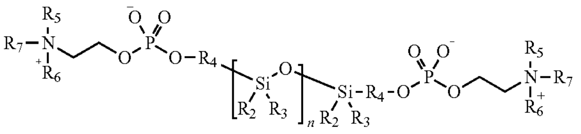

or the formula (VIII)

(VIII)

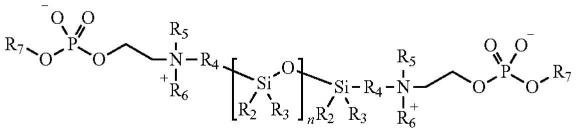

wherein:

$R_2$ and $R_3$ are the same or different groups selected from alkyl, trialkylsiloxy, silicone, alkoxy, alicyclic, and aromatic groups;

n is a number of repeat silicone units from 1 to 20,000 units;

$R_4$ is an alkylene or polyether or perfluorinated polyether linkage having up to 30 linking atoms;

$R_5$ and $R_6$ are the same or different alkyl, alkoxy, or aromatic groups or alicyclic rings containing 3 to 6 carbon atoms; and $R_7$ is an alkyl or alkoxy group containing 1 to 22 carbon atoms.

* * * * *